United States Patent [19]
Ghiretti

[11] Patent Number: 5,213,775
[45] Date of Patent: May 25, 1993

[54] DEVICE FOR PASSING OBJECTS BETWEEN TWO ENVIRONMENTS SEPARATED FROM EACH OTHER UNDER SEALED CONDITIONS, IN PARTICULAR FOR STERILIZATION OR PASTEURIZATION PLANTS

[75] Inventor: Ermes Ghiretti, Parma, Italy

[73] Assignee: Dall'Argine & Ghiretti S.r.l., Stradella di Collecchio, Italy

[21] Appl. No.: 717,519

[22] Filed: Jun. 19, 1991

[30] Foreign Application Priority Data

Jun. 21, 1990 [IT] Italy .............................. 46854 A/90

[51] Int. Cl.$^5$ .............................. B65G 35/00
[52] U.S. Cl. ..................... 422/295; 422/291; 422/297; 422/300; 414/219; 414/220
[58] Field of Search ............... 99/371, 477; 414/219, 414/220; 422/291, 295, 296, 297, 300; 222/368; 221/266

[56] References Cited

U.S. PATENT DOCUMENTS

| | | | |
|---|---|---|---|
| 1,530,516 | 3/1925 | Rarig | 198/468.1 |
| 2,585,472 | 2/1952 | Kennedy | 414/220 |
| 3,833,018 | 9/1974 | Brooks | 414/220 |
| 4,179,043 | 12/1979 | Fischer | 414/219 |
| 4,180,188 | 12/1979 | Aonuma et al. | 414/219 |
| 4,397,814 | 8/1983 | Darecchio | 422/111 |
| 4,565,305 | 1/1986 | Fischer et al. | 414/219 |
| 5,053,196 | 10/1991 | Ide et al. | 422/300 |

FOREIGN PATENT DOCUMENTS

| | | |
|---|---|---|
| 44116/85 | 6/1985 | Australia . |
| 709885 | 5/1968 | Belgium . |
| 0166716 | 6/1985 | European Pat. Off. . |
| 1509047 | 4/1978 | United Kingdom ............... 414/219 |

Primary Examiner—Robert J. Warden
Assistant Examiner—T. A. Trembley

[57] ABSTRACT

The device comprises an external fixed hollow casing (20) provided with a concave surface (21) of revolution about a central axis A and with two apertures (22') and (22") for passage of the objects, each aperture communicating with a respective environment; within the casing (20) there is provided a structure (10) rotatable about the axis A and in sealed engagement with the concave surface (21); the structure (10) comprises at least one blind chamber (11) for containing the objects; the structure (10) rotates to carry the objects which it receives from one aperture (22') to the other aperture (22"); in whatever angular position the structure (10) lies, it closes communication between the two apertures (22') and (22"); the device is applicable in particular to sterilization or pasteurization plants and represents an improvement to known device, and in particular achieves very high productivity.

9 Claims, 4 Drawing Sheets

DEVICE FOR PASSING OBJECTS BETWEEN TWO ENVIRONMENTS SEPARATED FROM EACH OTHER UNDER SEALED CONDITIONS, IN PARTICULAR FOR STERILIZATION OR PASTEURIZATION PLANTS

BACKGROUND OF THE INVENTION

This invention relates to the passage of objects under sealed conditions between two mutually separated environments, in particular for sterilization or pasteurization plants.

In certain types of such plants a chamber isolated from the external environment is provided in which the objects to be treated are placed. This chamber encloses an environment of hot steam under greater than atmospheric pressure in equilibrium with water at the same pressure and temperature.

An underlying chamber isolated from the external environment can also be provided, filled with colder water at the same pressure. The objects pass through the hotter chamber where they undergo sterilization or pasteurization, then pass through the lower chamber to be cooled and then extracted. In these plants, as in other different applications, there is the technical problem of introducing and extracting the objects into and from said chambers while maintaining the environments within the chambers isolated from the external environment, while taking account of the relatively high throughput of entering and leaving objects.

The known solutions to this technical problem are substantially based on the provision of a type of cylinder with a diameter much greater than its height, and comprising in its cylindrical surface various recesses each able to contain a single object. This cylinder is partially contained within the object treatment chamber and lies partially outside it. By rotating the cylinder a succession of objects are introduced into and extracted from the chamber.

However in these known devices the separation between the two environments is never very efficient, and fluid seepage from one environment to the other is inevitable. Moreover, each recess on entering and leaving carries with it a certain quantity of fluid (air, steam or water, from one environment to the other) and hence produces communication between the two environments. In addition, in known devices the objects are introduced and extracted one at a time in succession, and when the object dimensions change the introduction-extraction cylinder also has to be changed as the recesses must have substantially the same shape as the objects.

SUMMARY OF THE INVENTION

The object of the present invention is to obviate said drawbacks by a device able to introduce and extract the objects while maintaining the two environments effectively separated under sealed conditions, and comprising introduction/extraction compartments which can have a very large capacity so as to contain various objects, including objects of different diameters. Said object is attained by the device of the invention for passing objects between two environments separated from each other under sealed conditions.

BRIEF DESCRIPTION OF THE DRAWINGS

The invention is described in detail hereinafter with reference to the accompanying figures, which show a preferred embodiment thereof particularly suitable for application to a sterilization or pasteurization plant using hot pressurized steam and cooling water.

FIG. 2A is the same as FIG. 2 but with the internal structure 10 rotated through 90°.

DETAILED DESCRIPTION OF PREFERRED EMBODIMENT

Figure 6:
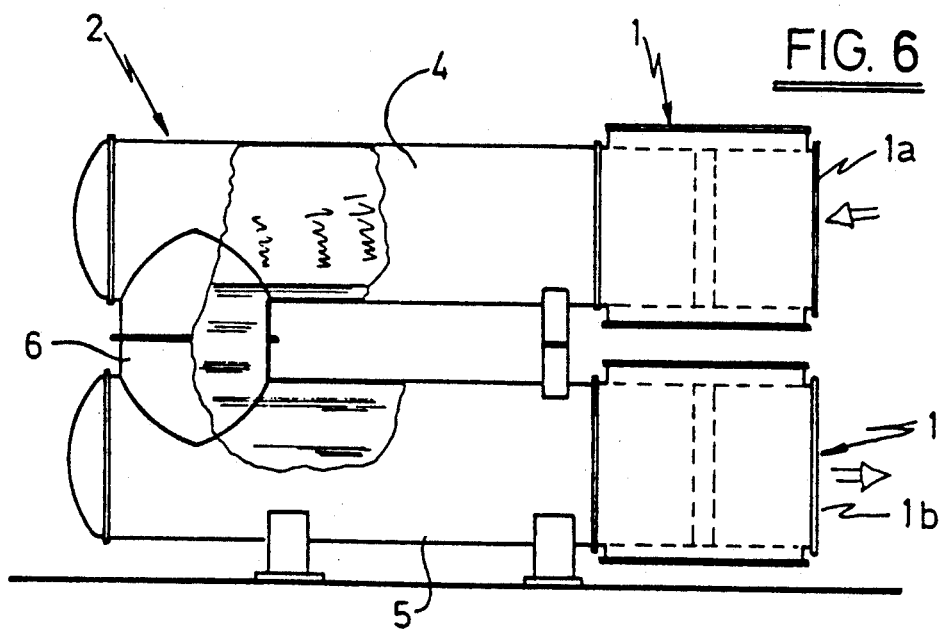
FIG. 6 is a vertical elevational schematic view of a plant to which two of the said devices of the preceding figures are applied.
Figure 4:
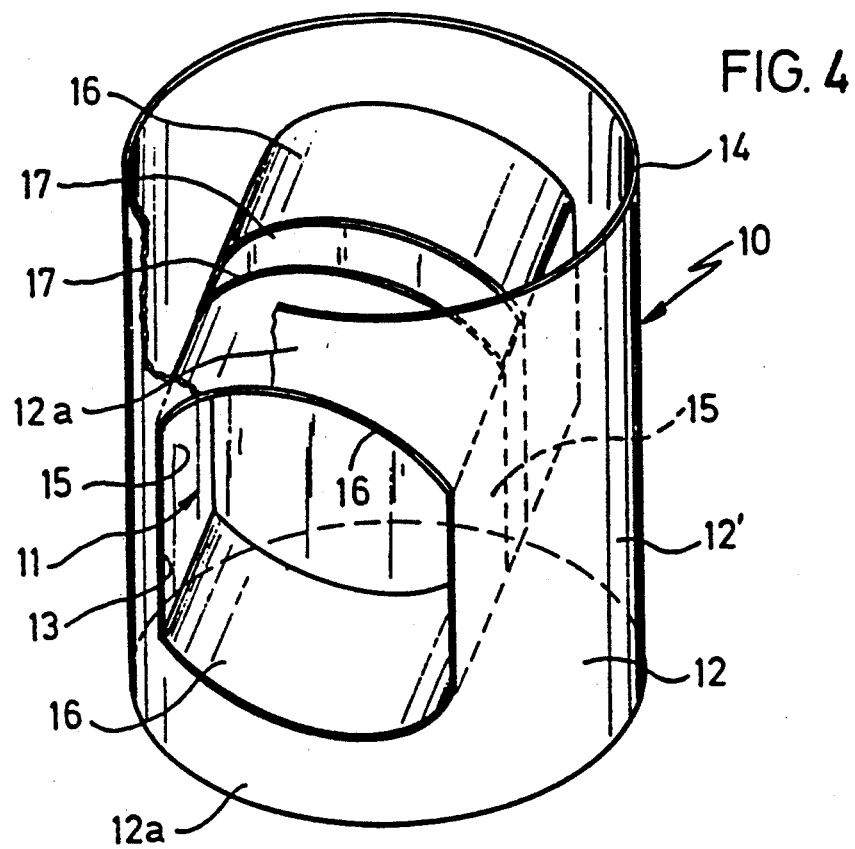
FIG. 4 is a perspective view of the internal structure 10 of the preceding figures.
Figure 5:
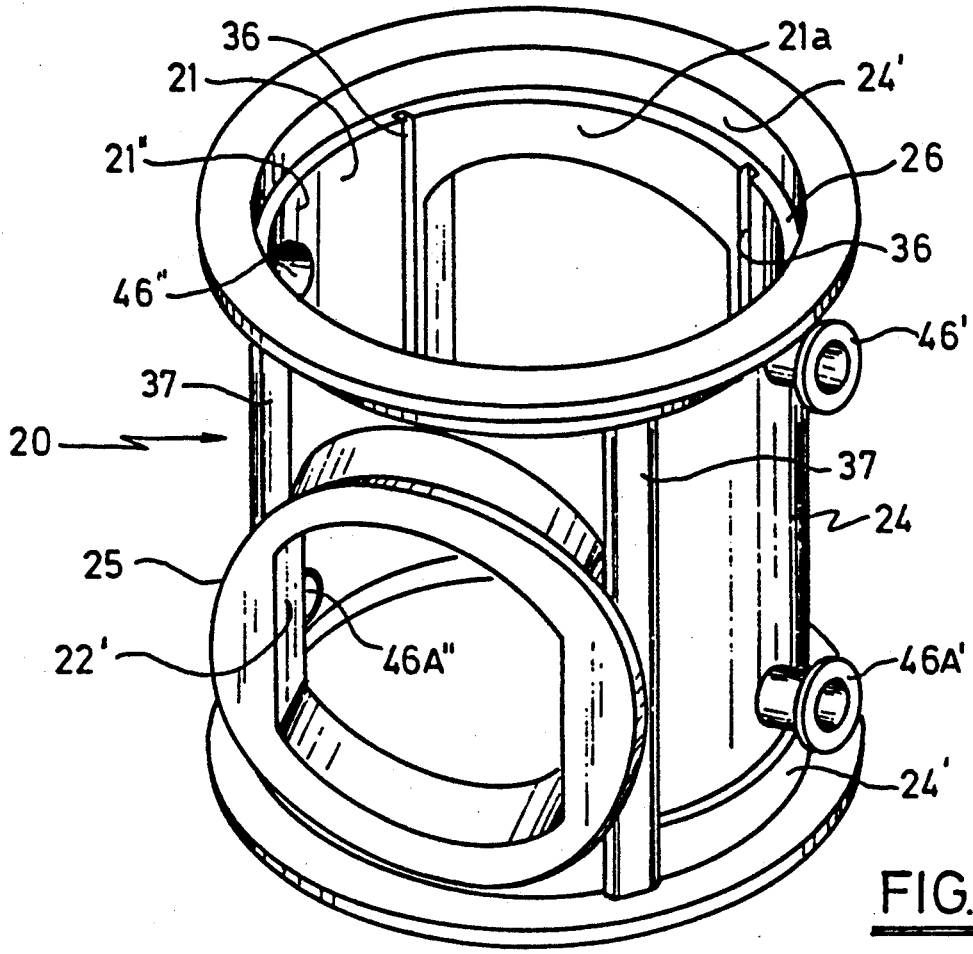
FIG. 5 is a perspective view of the outer casing 20 of the preceding figures.

In the applicational example illustrated in FIG. 6, the device of the invention, indicated overall by 1, is used for passing objects between the external environment and the internal environment of a sterilization or pasteurization plant, these environments to be kept separated under hermetic seal.

The device 1 comprises a hollow outer casing 20 provided with a concave surface 21 representing a surface of revolution about a central vertical axis A. The surface 21 is provided, for passage of the objects, with two apertures 22' and 22" each communicating with a respective environment. Specifically, the aperture 22' communicates with the external environment whereas the aperture 22" communicates with the environment internal to the plant 2. Inside the casing 20 there is provided a structure 10 rotatable about the axis A and in sealed engagement with the concave surface 21. Said structure 10 possesses one or more blind chambers 11 for containing the objects. Said chambers 11 open into the lateral surface of the structure 10, and following rotation of the structure 10 they come face to face with only one aperture 22' or 22" at a time. Moreover, in whichever angular position it lies, the structure 10 closes communication between the apertures 22' and 22".

Figure 2:
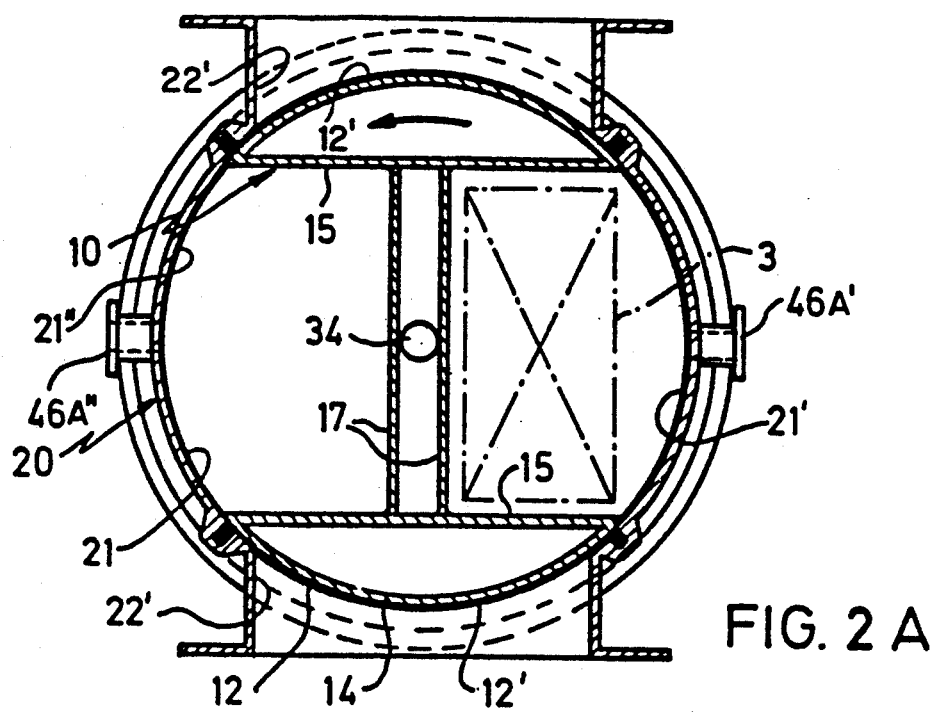
FIG. 2 is a plan section on the line II—II of FIG. 1.
Figure 2:
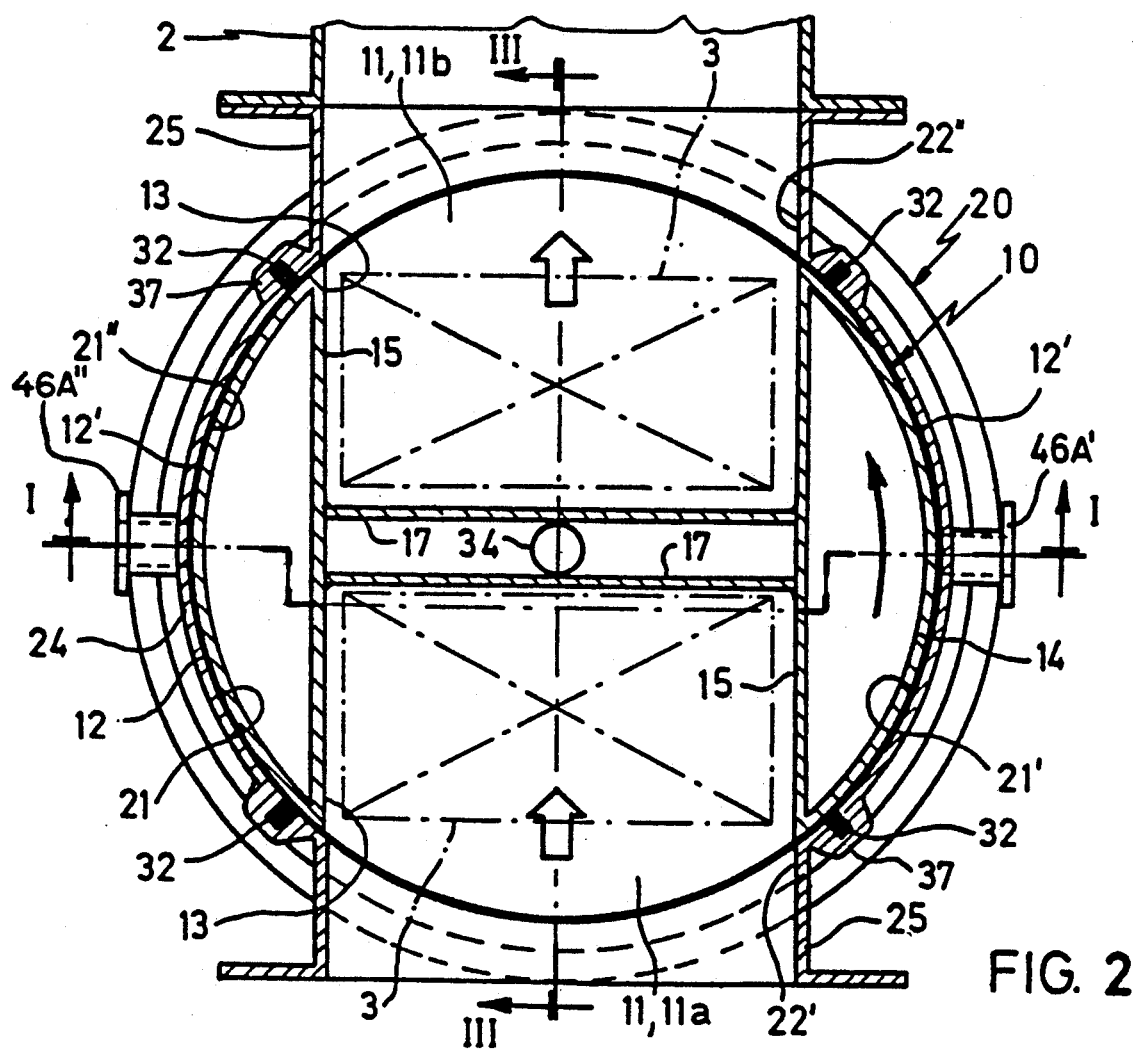

Specifically, the internal structure 10 comprises two mutually separated blind chambers 11 positioned 180° apart in the plane of rotation of the structure 10 (see FIG. 2). The apertures 22' and 22" of the casing 20 are centered on the same axis perpendicular to the axis A. The internal structure 10 comprises a convex surface in the form of a right circular cylinder into which the chambers 11 open. The surface 21 is also of circular cylindrical shape and (except for the necessary constructional clearances for accommodating material expansion) matches the convex surface 12 of the internal structure 10. The maximum angular dimension of the mouths 13 with reference to the overall cross-section (FIG. 2) is less than the angular dimension of the two portions 21' and 21" of the concave surface 21 intermediate between the two apertures 22' and 22".

Figure 3:
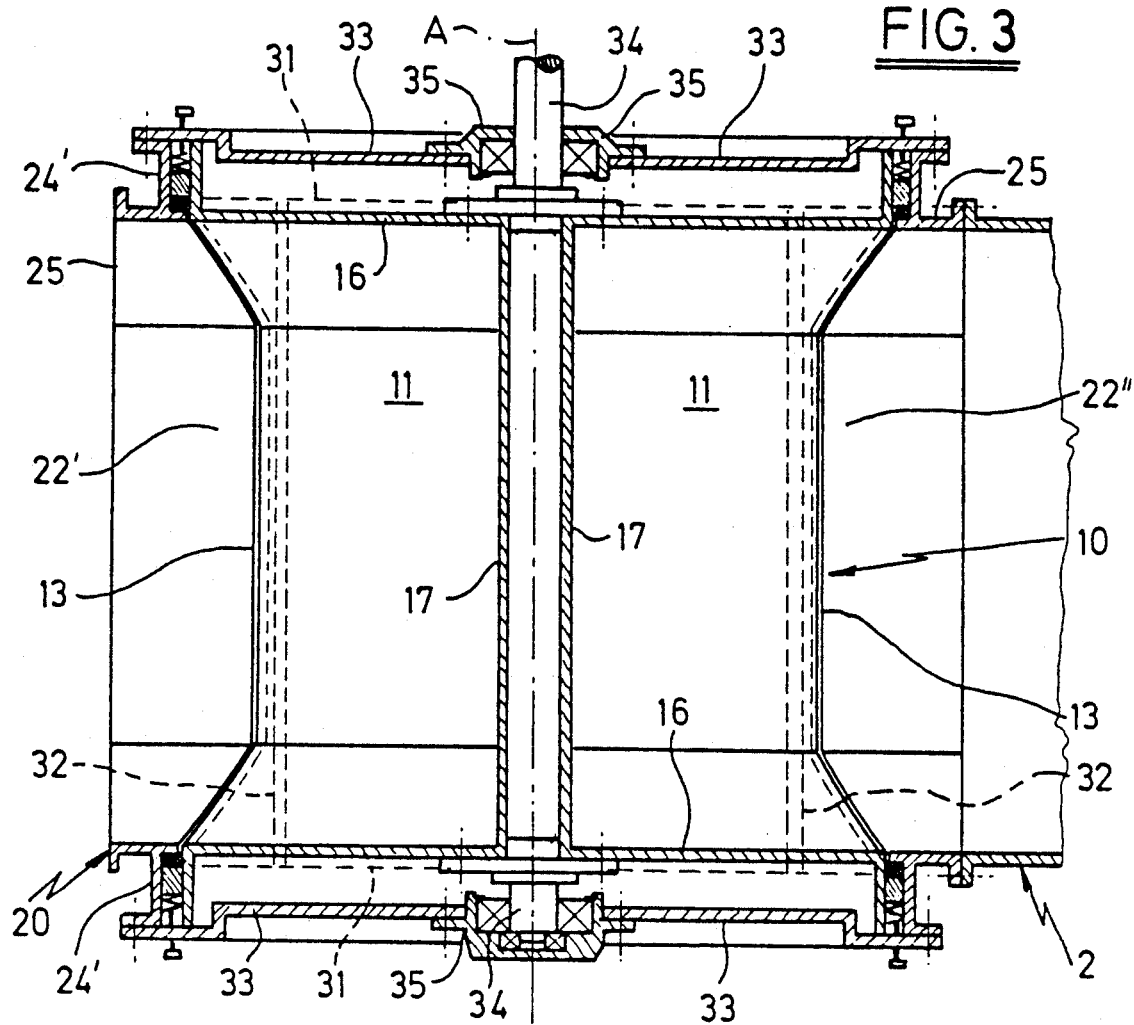
FIG. 3 is a vertical elevational section on the line III—III of FIG. 2.

The mouths 13 of the chamber 11 are substantially identical and match the apertures 22' and 22" of the casing 20. The mouths 13 and apertures 22' and 22" have a maximum height less than the height of the surface 12 and of the surface 21 respectively, and are located in a centered position such that above and below them there is defined a strip of cylindrical surface 12 and 21 respectively (said strips are indicated in the figures by 12a and 21b respectively). When the internal structure 10 is in a position such that the mouths 13 mate with the apertures 22' and 22" (position shown in FIGS. 1, 2 and 3), the two intermediate portions 21' and 21" mate with respective intermediate portions 12' of the surface 12 (defined between the two mouths 13) and the surface strips 21a mate with the strips 12a. In contrast, when the structure 10 has been rotated through 90° from the said position (angular position intermediate between the two apertures 22' and 22") the blind chambers 11 are closed by respective intermediate portions 12' of the surface 12, whereas the apertures 22' and 22" are closed by the portions 12' of the convex surface 12 (position shown in FIG. 2A). To form the hermetic seal between the mutually engaging surfaces 12 and 21 there are provided two lines of circumferential gaskets 31 and four lines of axial gaskets 32. The lines 31 are positioned above and below the apertures 22' and 22" respectively (and hence above and below the mouths 13). In other words, each line 31 lies in a plane perpendicular to the axis A, between the uninterrupted circular cylindrical surface band 21 defined by the two intermediate portions 21' and 21" and strips 21a on one side, and the uninterrupted circular cylindrical surface band 12 defined by the intermediate portions 12' and strips 12a. The gasket lines 32 are rectilinear and vertical and are positioned to the outside of but in proximity to the two apertures 22' and 22". The lower and upper ends of the lines 32 join the lines 31. The angular distance between each axial line 32 and the line closest to it is greater than the maximum angular dimension of the mouth 13 and of the apertures 22' and 22". In the illustrated embodiment the surface 21 is defined by a metal wall of right circular cylindrical shape in which the apertures 22' and 22" are formed. These are provided with two flanged mouths 25 arranged to be fixed to the plant 2 or other equipment. The surface 12 is defined by a metal wall of circular cylindrical shape within which the two blind chambers 11 are provided. Each of these is defined by two vertical flat side walls 15, two arched walls 16 at the roof and floor of the chamber and a vertical rear wall 17. The two walls 17 of the two chambers 11 are separated from each other by an empty interspace along which the the ideal axis of rotation A passes. The structure 10 is completely surrounded by the wall 24. This is closed upperly and lowerly by respective covers 33. The structure 10 rotates on two pins 34 coaxial to the axis A. Said pins 34 are rotatably supported at the respective covers 33 by suitable supports 35 and are fixed respectively to the top and bottom of the interspace formed by the two walls 17.

The lower support 35 also supports the axial thrusts. The upper pin 34 is connected to known motor means (not shown) to rotate the structure 10.

Figure 8:
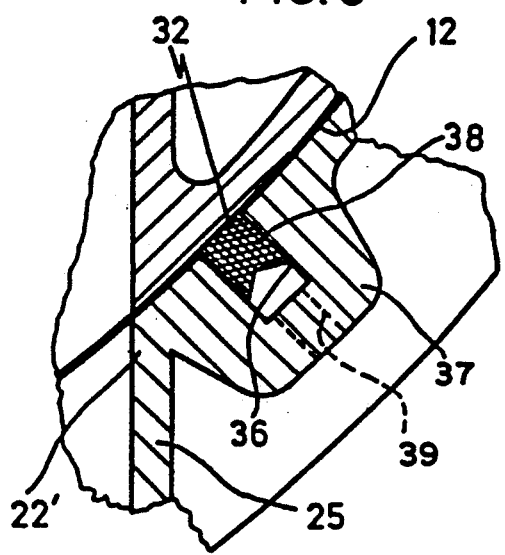
FIG. 8 is an enlarged detail of FIG. 2.

Each of the four gasket lines 32 (shown in section in FIG. 8) comprises an axial grove 36 formed in a respective axially extending ridge 37 on the wall 24. The groove 36 extends throughout the entire height of the line 32 and is open inwards, ie it "sees" the surface 12. The groove 36 holds an element 38 of material suitable for forming a seal, and extending axially along the entire gasket line 32. Said seal element 38 can undergo relatively small movements in a radial direction within the groove 36. On the element 38 there act means for providing the element with a thrust distributed substantially uniformly over its entire height, to urge the element 38 against the surface 12 of the internal structure 10.

This thrust presses the element 38 against the (mobile) surface 12 and against the side walls of the groove 36, to hence produce the sealing action.

Said thrust means can be of various types. For example a pressurized fluid can be fed from the outside into the groove 36 through holes 39. Alternatively a rod with various cam portions can be provided which when rotated presses the element 38.

Said thrust means are operated only when the surface 12 is in front of the seal element 38. In contrast, when it is passing the mouth 13 of a chamber 11, the element 38 is not subjected to thrust.

Figure 7:
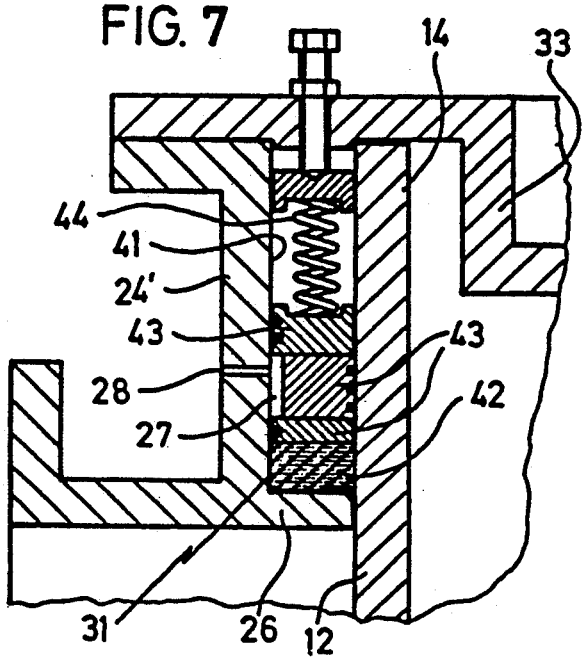
FIG. 7 is an enlarged detail of FIG. 1.

Each circumferential gasket line 31 comprises an annular chamber 41 with an axially extending cross-section (shown in FIG. 7), formed between the surfaces 21 and 12 of the casing 20 and structure 10 respectively. The chambers 41 lie between the respective upper and lower end portion of the cylindrical wall 14 and the corresponding upper and lower end portion 24' of the cylindrical wall 24. To form the chambers 41 the end portions 24' have a greater diameter than the central band of the wall 24. The chamber 41 is closed at one end by a radial projection 26 from the wall 24.

On the projection 26, the chamber 41 contains an annular element 42 of material suitable for forming a seal and extending along the entire circumferential line 31. Said element 42 is arranged to form a seal between the casing 10 and the structure 20. Some rigid rings are placed in the chamber 41 against the seal element 42. Various thrust means 44 are also provided (comprising adjustable precompressed elastic springs) to urge the rings 43 against the seal element 42 and press this against the radial projection 26. The thrust presses the element 42 against the projection 26 and against the two side walls of the chamber 41, to produce the sealing action.

To increase the sealing action, between one or more rings 43 and a side wall of the chamber 41 there is provided an interspace 27 which is kept filled with liquid introduced from the outside through one or more holes 28. In contrast to the axial gasket lines 32, the circumferential lines 31 are always pressed by the thrust means 44. This is because the surface 12 is always facing the seal element 42. In operation, the structure 10 rotates (in a constant direction) so that during one complete revolution it moves each chamber 11 into four different main positions spaced apart by 90°, namely a first position in which one chamber 11 (11a) faces the aperture 22' (position shown in FIG. 2), a second position in which chamber 11a is in an intermediate position between the two apertures 22' and 22" (FIG. 2A) and is closed by the intermediate portion 21' of the surface 21, a third position in which the chamber 11a faces the aperture 22", and a fourth position in which the chamber 11a is in an intermediate position between the two apertures 22' and 22" and is closed by the intermediate portion 21".

During this rotation the other chamber 11 (indicated by 11b) is always 180° from the chamber 11a, so that when the chamber 11a is in the first position the chamber 11b is in the third position, when the chamber 11a is in the second position the chamber 11b is in the fourth position, and so on.

In the described positions, all the gasket lines 32 are in operation. The two apertures 22' and 22" are always separated from each other under sealed conditions by the action of the gaskets 31 and 32. In the second and fourth positions the chambers 11 are also separated under sealed conditions from the apertures 22' and 22".

The device of the invention also comprises means which when the chamber 11 is in said intermediate positions (second and fourth position) are able to reproduce in it the same environmental conditions as in the environment towards which the chambers 11 are respectively directed. In detail, the objects (indicated overall by 3) are initially inserted through the aperture 22' and into the chamber 11a when this in the first position. At the same time other objects 3 present in the chamber 11b are extracted from the chamber and introduced into the internal environment of the plant 2 through the aperture 22". Said objects 3 can be either a group of objects or a single large object. Basically, the objects 3 can occupy the entire volume of the chambers 11.

The structure 10 is then rotated through 90° and the same environmental conditions as the internal environment of the plant 2 are created in the chamber 11a. At the same time the environmental conditions of the external environment are reproduced in the empty chamber 11b. The structure 10 is then rotated through a further 90° and the chamber 11a comes face to face with the aperture 22'. The objects 3 are then extracted and introduced into the plant 2. At the same time other objects 3 are introduced into the chamber 11b through the aperture 22' and the aforedescribed cycle is repeated, the chamber 11a now being replaced by the chamber 11b and vice versa.

A typical application of the device of the invention is as an entry device to a chamber 4 forming part of a sterilization or pasteurization plant 2, containing steam and hot water under pressure. A plant of this type is shown by way of example in FIG. 6 in which the entry device to the chamber 4 is indicated by 1a.

The plant 2 also comprises a chamber 5 filled with cooling water, to the chamber 5 there being applied a further device 1, indicated by 1b, for the exit of the objects 3. The two chambers 4 and 5 are superposed on each other and communicate via a wide duct 6 of vertical axis filed with water which is hot at the top but colder at the bottom.

Figure 1:
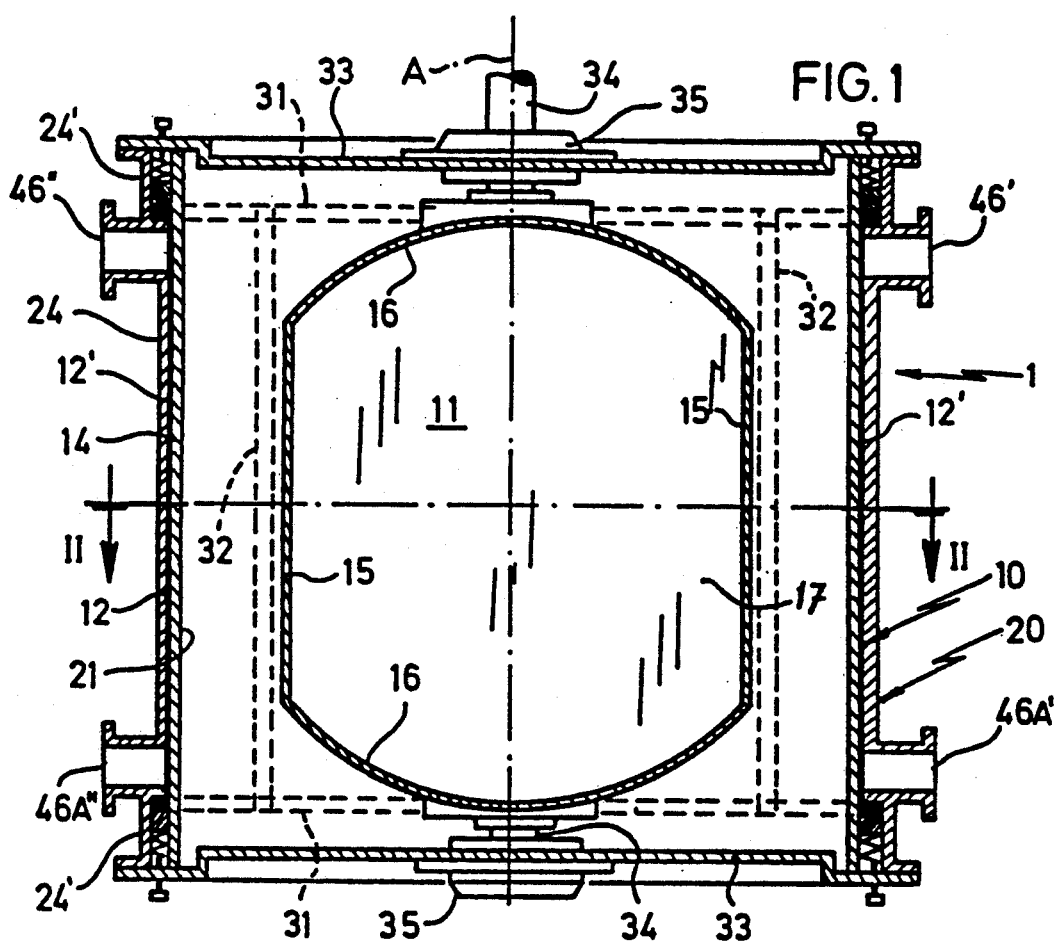
FIG. 1 is a vertical elevational section on the line I—I of FIG. 2.

Each device 1 comprises two pairs of mouths 46' and 46" respectively, applied to the wall 24 in the middle region of the two portions 21' and 21". One of the mouths 46' and 46" is in a lower position and the other is in a higher position. Thus, as shown in FIG. 1, there is an upper mouth 46' and a lower mouth 46A', as well as an upper mouth 46" and a lower mouth 46A".

In the device 1a, when a chamber 11 is in the intermediate position directed towards the environment within the chamber 4 (i.e. in said second position), pressurized hot water is fed into the chamber 11 from the chamber 4 through the lower mouth 46A'. At the same time the air initially present in the chamber 11 is evacuated through the upper mouth 46'.

When the chamber 11 is in the intermediate position directed towards the external environment (i.e. in said fourth position), cold water is fed into the chamber 11 through the upper mouth 46". This water cools and condenses the steam initially present in the chamber 11 (received from the chamber 4) and leaves through the lower mouth 46A" to hence reproduce in the chamber 11 the conditions of the external environment.

In the device 1b (applied to the chamber 5), when the two chambers 11a and 11b are in the two intermediate positions (second and fourth position), the water present in that chamber 11 directed towards the external environment (water received from the chamber 5) is withdrawn via the lower mouth 46A" and is fed via the lower mouth 46A' into that chamber 11 directed towards the environment of the chamber 5.

The capacity of the blind chambers 11 can be very large and the device of the invention can therefore have a very high operating potential. The sealed separation between the two environments is very efficient. In addition, the blind chambers 11 do not entrain with them the atmosphere present in the environment from which they originate. Thus the two environments are effectively separated form each other. Numerous modifications of a constructional and applicational nature can be applied to the device of the invention but without leaving the scope of the inventive idea as hereinafter claimed.

I claim:

1. A device for passing objects between two environments separated from each other under sealed conditions, in particular for sterilization or pasteurization plants, comprising:

a fixed hollow outer casing (20) provided with a concave surface (21) of revolution about a central A and also provided, for the passage of objects, with two apertures (22') and (22") each communicating with a respective environment;

inside said fixed hollow outer casing (20), an internal structure (10) rotatable about said central axis (A) and in sealed engagement with the concave surface (21) of the fixed hollow outer casing (20), and provided with at least one chamber (11), having a mouth (13), to contain the objects and opening into a convex surface (12) of said internal structure (10);

said internal structure (10), in whichever angular position it lies, closing the communication between the two apertures (22') and (22") of the fixed hollow outer casing (20);

said chamber (11) facing only one of said apertures (22') and (22") at a time following rotation of the internal structure (10), said chamber when in intermediate angular positions between said apertures (22') and (22") being closed by a respective first and second intermediate portion (21'), (21") of concave surface (21) of the fixed hollow outer casing (20), and said two apertures (22') and (22") being closed by the convex surface (12) of the internal structure (10), means being provided for reproducing in the chamber (11), when this is in said intermediate positions, the same environmental conditions as the environment toward which the chamber (11) is directed, and gasket means (31, 32) being provided for achieving a hermetic seal between the convex surface (12) of the internal structure (10) and the concave surface (21) of the fixed hollow outer casing (20).

2. A device as claimed in claim 1, wherein the internal structure (10) comprises two said chambers (11) with each chamber being located in a separate portion of the internal structure (10), the two apertures (22') and (22") in the fixed hollow outer casing (20) being centered on the same axis perpendicular to the central axis of rotation (A).

3. A device as claimed in claim 2, wherein:
said internal structure (10) comprises a convex surface (12) in the form of a circular cylinder, into which each of said chambers (11) opens;
said fixed hollow outer casing (20) comprises a concave surface (21) in the form of a circular cylinder, substantially equal to and arranged to receive as an exact fit the convex surface (12) of the internal structure (10);
a maximum angular dimension of each of the mouths (13) of the chambers (11) being less than the angular dimension of the two portions (21') and (21") of the concave surface (21) intermediate between the two apertures (22') and (22");
the mouths (13) of the chambers (11) being substantially equal and arranged to mate with the two apertures (22') and (22");
the mouths (13) of the chambers (11) and said two apertures (22') and (22") having a maximum height less than the height of the convex surface (12) and of the concave surface (21) and being arranged such that above and below them here are defined a strip of convex cylindrical surface (12a) and of concave cylindrical surface (21a) respectively.

4. A device as claimed in claim 3, wherein said gasket means for achieving a hermetic seal between the convex surface (12) of the internal structure (10) and the cylindrical surface (21) of the fixed hollow outer casing (20) includes:
two circumferential gasket means (31) positioned above and respectively below the two apertures (22') and (22") and the mouths (13) of the internal structure (10) and fixed hollow outer casing (20);
four axial gasket means (32) positioned to the outside of and in proximity to the two apertures (22') and (22"), the ends of which join to the two circumferential gasket means (31);
the angular distance between adjacent axial gasket means (32) being greater than the maximum angular dimension of the mouths (13) of the chambers (11) and of the two apertures (22') and (22").

5. A device as claimed in claim 4, wherein said four axial gasket means (32) each comprise:
an inwardly open axial groove (36) provided in the fixed hollow outer casing (20) and extending throughout the entire height of the four axial gasket means (32);
a seal element (38) positioned within the axial groove (36) and extending axially through the entire four axial gasket means (32), said seal element (38) being able to move radially through short movements within the axial groove (36);
means for applying to the seal element (38) an axial thrust distributed substantially uniformly throughout its entire height, and directed such as to press the seal element (38) against the convex surface (12) of the internal structure (10).

6. A device as claimed in claim 4, wherein said two circumferential gasket means (31) each comprise:
an annular chamber (41) with an axially extending cross-section, formed between the surfaces of the internal structure (10) and fixed hollow outer casing (20) and closed at one end by a radial projection (26) from the fixed hollow outer casing (20);
an annular seal element (42) positioned within said annular chamber (41), against said radial projection (26) and arranged to form a seal between the fixed hollow outer casing (20) and the internal structure (10);
one or more rigid rings (43) positioned within said annular chamber (41) against said annular seal element (42), on the opposite side to that on which the radial projection (26) is situated;
thrust means to urge said one or more rigid rings (43) against the annular seal element (42);
between said one or more rigid rings (43) and the annular chamber (41) there being provided an interspace (27) which is kept filled with liquid.

7. A device as claimed in claim 1 wherein said device is connected to an inlet of a portion (4) of a sterilization or pasteurization plant containing steam and hot water under pressure and further comprising:
a first mouth (46A') being situated in a lower region of said first intermediate portion (21'),
feeding means for feeding pressurized hot water from the sterilization or pasteurization plant through said first mouth (46A') when the chamber (11) is in the intermediate position directed towards the internal environment of the portion (4), and
a second mouth (46') situated in an upper region of said first intermediate portion (21') so that air initially present in the chamber (11) can be evacuated.

8. A device as claimed in claim 1 wherein said device is applied to the inlet of a portion (4) of a sterilization or pasteurization plant containing steam and hot water under pressure and further comprising
a first mouth (46") being situated in an upper region of said second intermediate portion (21") of said concave surface (21),
feeding means for feeding cold water into said chamber through said first mouth (46") when the chamber (11) is in the intermediate position directed towards the external environment and
a second mouth (46A") situated in a lower region of said second intermediate portion (21") so that water and condensed steam present in the chamber (11) can leave.

9. A device as claimed in claims 1 or 2 wherein said device is connected to the outlet of a portion (5) of a sterilization or pasteurization plant containing cooling water under pressure, and further comprising
fluid handling means operative when two chambers are in the intermediate position to withdraw water present in that chamber (11) directed toward the external environment and feed the water into that chamber (11) directed towards an internal environment of the plant.

* * * * *